United States Patent [19]

Tessier et al.

[11] Patent Number: 4,849,449
[45] Date of Patent: Jul. 18, 1989

[54] NOVEL CYCLOPROPANE CARBOXYLATES

[75] Inventors: Jean Tessier, Vincennes; Jean-Pierre DeMoute, Montreuil; Joseph Cadiergue, Aulnay Sous Bois, all of France

[73] Assignee: Roussel Uclaf, Paris, France

[21] Appl. No.: 939,635

[22] Filed: Dec. 9, 1986

[30] Foreign Application Priority Data

Dec. 10, 1985 [FR] France .................. 85 18226
Jul. 9, 1986 [FR] France .................. 86 09997

[51] Int. Cl.⁴ .................. C07C 121/46; A01N 37/34
[52] U.S. Cl. .................. 514/521; 546/301; 548/187; 548/204; 548/312; 548/479; 549/420; 549/499; 558/405; 558/407; 560/124
[58] Field of Search .................. 558/407; 514/520, 531, 514/521; 560/124

[56] References Cited

U.S. PATENT DOCUMENTS

| | | | |
|---|---|---|---|
| 4,024,163 | 5/1977 | Elliott et al. | 558/407 X |
| 4,248,888 | 2/1981 | Szekely et al. | 514/531 |
| 4,299,972 | 11/1981 | Kovacs et al. | 560/124 |
| 4,378,372 | 3/1983 | Ackermann et al. | 558/407 X |
| 4,423,243 | 12/1983 | Jautelat et al. | 558/407 X |
| 4,457,940 | 7/1984 | Katsuda et al. | 558/407 X |
| 4,458,090 | 7/1984 | Fumio et al. | 558/407 X |
| 4,464,391 | 8/1984 | Elliott et al. | 558/407 X |
| 4,468,521 | 8/1984 | Fumio et al. | 558/407 X |
| 4,611,010 | 9/1986 | Schwarz et al. | 558/407 X |
| 4,670,464 | 6/1987 | Doyle et al. | 558/407 X |
| 4,681,969 | 7/1987 | Williams et al. | 558/407 |

Primary Examiner—Joseph Paul Brust
Attorney, Agent, or Firm—Bierman and Muserlian

[57] ABSTRACT

Novel stereoisomers or mixtures of stereoisomers of compounds of the formula

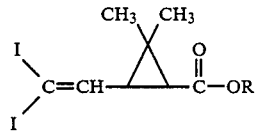

wherein R is the residue of an alcohol used in the pyrethrinoid field having remarkable pesticidal properties and being surprisingly stable.

8 Claims, No Drawings

NOVEL CYCLOPROPANE CARBOXYLATES

STATE OF THE ART

French Pat. No. 2,185,612 describes the chlorinated and brominated analogs of the esters of formula I but the diiodo compounds of formula I are not described therein. The carbon tetraiodide starting material which would be necessary in the process described in the said patent is not very stable and is therefore difficult to handle. Moreover, diiodo products would be expected by one skilled in the art to be unstable. Related prior art includes U.S. Pat. No. 4,024,163, British Pat. No. 2,058,784 and German Pat. No. 2,941,332.

OBJECTS OF THE INVENTION

It is an object of the invention to provide the stereoisomers and mixtures thereof of the diiodovinyl compounds of formula I and to provide a process for their preparation.

It is another object of the invention to provide novel pesticidal compositions and to provide a novel method of combatting pests.

These and other objects and advantages of the invention will become obvious from the following detailed description.

THE INVENTION

The novel compounds of the invention are the stereoisomers or mixtures of stereoisomers of compounds of the formula

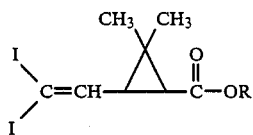

wherein R is the residue of an alcohol used in the pyrethrinoid field. Surprisingly, the compounds of formula I are stable and endowed with excellent pesticidal properties.

Examples of R are (a) alkyl of 1 to 8 carbon atoms, (b) benzyl, (c) a compound of the formula

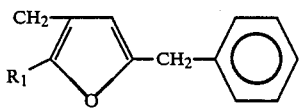

wherein $R_1$ is hydrogen or methyl, (d) a group of the formula

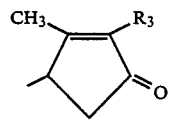

wherein $R_3$ is an organic aliphatic radical of 2 to 6 carbon atoms and at least one carbon-carbon unsaturation and more particularly,
—$CH_2$—$CH$=$CH_2$
—$CH_2$—$CH$=$CH$—$CH_3$,
—$CH_2$—$CH$=$CH$—$CH_2$—$CH_3$,
—$CH_2$—$CH$=$CH$—$CH$=$CH_2$,
—$CH_2$—$C$≡$CH$, (e) a group of the formula

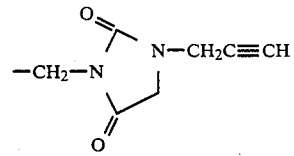

wherein B is C=O or oxygen and $R_4$ is hydrogen, methyl, —C≡N, —C≡CH or $$-\underset{\underset{S}{\|}}{C}-NH_2,$$

(f) a group of the formula

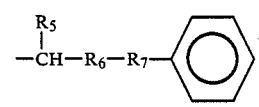

(g) a group of the formula

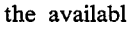

(h) a group of the formula

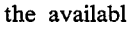

wherein $R_5$ is hydrogen or —CN, $R_6$ is a thiazolyl in which the link $$\underset{-CH-}{\overset{R_5}{|}}$$

can be at any of the available positions and $R_7$ is —$CH_2$— or oxygen;

(i) a group of the formula

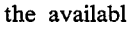

(j) a group of the formula

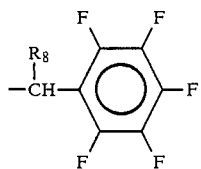

wherein R$_8$ is hydrogen or —CN,
(k) a group of the formula

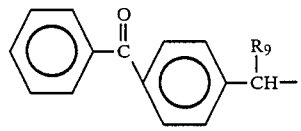

wherein R$_9$ is hydrogen or —CN,
(l) a group of the formula

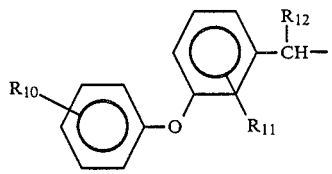

wherein R$_{12}$ is hydrogen, methyl, ethynyl or cyano and R$_{10}$ and R$_{11}$ are different from each other and are hydrogen, fluorine, chlorine or bromine;
(m) a group of the formula

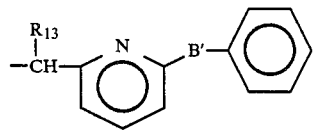

wherein R$_{13}$ is hydrogen, methyl, ethynyl or cyano and B' is oxygen or sulfur,
(n) a group of the formula

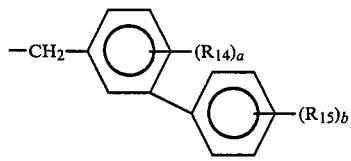

wherein R$_{14}$ is halogen, alkyl of 1 to 6 carbon atoms or trifluoromethyl, R$_{15}$ is halogen, alkyl of 1 to 6 carbon atoms, an alkoxy of 1 to 6 carbon atoms or trifluoromethyl, a is 0, 1, 2, 3 or 4 and b is 0, 1, 2, 3, 4 or 5.

In the compounds of the invention, when R is a linear or branched alkyl of 1 to 8 carbon atoms, it is preferably methyl, ethyl, linear or branched propyl, linear or branched butyl, linear or branched pentyl, linear or branched hexyl, or linear or branched octyl.

Among the preferred compounds of formula I in all their stereo-isomeric forms or in the form of mixtures of stereo-isomers are those wherein R has the formula

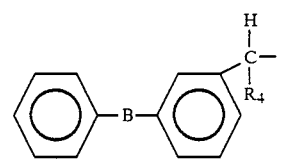

wherein B is C═O or oxygen and R$_4$ is hydrogen, methyl, —C≡N, —C≡CH, or $$-\underset{\underset{S}{\|}}{C}-NH_2,$$

and particularly the group

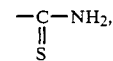

those wherein R has the formula

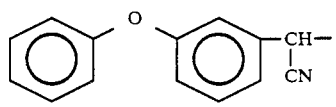

wherein R$_{12}$ is hydrogen, methyl, ethynyl or cyano and R$_{10}$ and R$_{11}$, different from each other, are hydrogen, fluorine, chlorine or bromine, and particularly the group of the formula

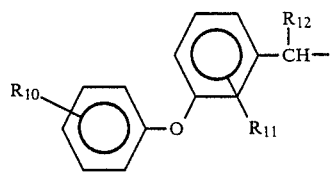

those wherein R has the formula

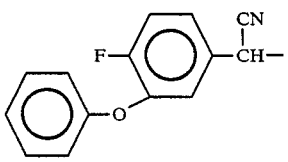

wherein R$_{13}$ is hydrogen, methyl, ethynyl or cyano and B' is oxygen or sulfur, and particularly the group

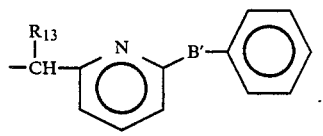

those wherein R has the formula

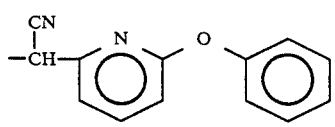

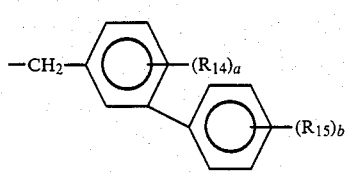

wherein $R_{14}$ is halogen, alkyl of 1 to 6 carbon atoms or trifluoromethyl, $R_{15}$ is halogen, alkyl of 1 to 6 carbon atoms, alkoxy of 1 to 6 carbon atoms or trifluoromethyl, a is 0, 1, 2, 3 or 4 and b is 0, 1, 2, 3, 4 or 5 and particularly the group

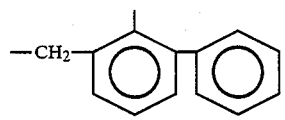

Among the specific preferred compounds of the invention are: (S) cyano-(3-phenoxy-4-fluorophenyl)-methyl 1R, cis 2,2-dimethyl-3-(2,2-diiodoethenyl)-cyclopropane-carboxylate and (S) cyano 1-(3-phenoxy-4-fluorophenyl)-methyl 1R, cis 2,2-dimethyl-3-(2,2-diiodoethenyl)-cyclopropane-carboxylate and the (R) cyano-1-(3-phenoxy-4-fluorophenyl)-methyl-1S, cis 2,2-dimethyl-3-(2,2-diiodoethenyl)-cyclopropane-carboxylate in a 50-50 mixture.

The Wittig reaction described in French Pat. No. 2,185,612 was not usable for the preparation of the diiodovinyl compounds of formula I since the reaction useful with carbon tetrachloride and carbon tetrabromide was not satisfactory with carbon tetraiodide.

Until recently, 1,1-diiodoalkenes were an almost unknown class of compounds since only diiodomethylenecyclohexane had been prepared with boron as an intermediate [Ganina et al., J. Chem. Soc. Commun. (1985), p. 1985]. Ganina et al carried out for the first time the conversion of aliphatic and aromatic aldehydes into diiodo-alkenes by a Wittig reaction using triphenylphosphine and carbon tetraiodide. However, the reaction is very delicate and requires the use of very pure carbon tetraiodide at close to 0° C. Applicants have now found that the Ganina et al reaction can be used to convert 3-formyl-2,2-dimethylcyclopropane carboxylic aldehydes into 2,2-dimethyl-3-(2,2-diiodoethenyl)-cyclopropane-carboxylic acid.

The novel process of the invention for the preparation of the compounds of formula I comprises reacting a stereoisomer or mixtures thereof of a compound of the formula

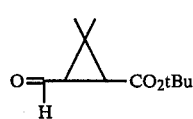

with tetraiodomethane and triphenyl phosphine in an organic solvent to obtain a compound of the formula

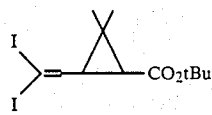

reacting the latter with p-toluene sulfonic acid in an organic solvent to obtain a compound of the formula

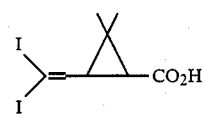

which may be converted into a functional acid derivative such as acid chloride, anhydride or mixed anhydride and the acid of formula IV or a functional derivative of thereof is reacted with an alcohol of the formula

R—OH or a functional derivative of this alcohol to obtain the corresponding product of the formula

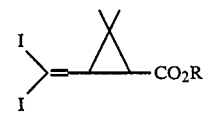

In a preferred mode of the process of the invention, the organic solvent in which tetraiodomethane and triphenyl phosphine are reacted with a compound of formula II is a chlorinated aliphatic solvent such as methylene chloride and the organic solvent in which p-toluene sulfonic acid is reacted with a compound of formula III is an aromatic solvent such as benzene, toluene or xylene. The preferred functional derivative of the acid is the acid chloride which reacts with the alcohol R—OH in the presence of a tertiary base and the acid of formula IV is reacted with the alcohol ROH in the presence of dicyclohexylcarbodiimide or of diisopropylcarbodiimide and 4-dimethylaminopyridine.

In a modification of the process of the invention for the preparation of a compound of formula I, a compound of the formula

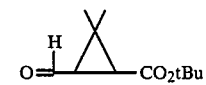

is reacted with tetraiodomethane, triphenylphosphine and zinc in organic solvent to obtain a compound of the formula

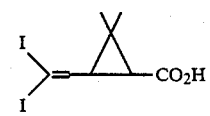

and then the synthesis proceeds as above.

In a preferred mode of the said process, the organic solvent in which tetraiodomethane, triphenylphosphine and zinc are reacted with a compound of formula II is a chlorinated aliphatic solvent such as methylene chloride.

The novel pesticidal compositions of the invention are comprised of a pesticidally effective amount of at least one stereoisomer or mixtures thereof of formula I and an inert carrier. The compositions are useful for combatting vegetation parasites, premises parasites and warm-blooded animals parasites and are useful particularly to combat insects, nematodes and vegetation and animal acariens.

In compositions intended for agricultural use and for use in premises, the active compounds of formula I may have added to them one or more other pesticide agents and these compositions may be in the form of powders, granules, suspensions, emulsions, solutions, solutions for aerosols, combustible strips, baits or other preparations normally employed for the utilization of this type of compound.

In addition to the active principle, the compositions generally contain a vehicle and/or a non-ionic surface active agent to ensure a uniform dispersion of the substances which form the mixture. The vehicle utilized can be a liquid such as water, alcohol, hydrocarbons or other organic solvents, a mineral, animal or vegetable oil, a powder such as talc, clays, silicates, kieselguhr or a combustible solid.

The products of formula I can be used particularly to combat insects in the agricultural field, to combat, for example, aphids, larvae of lepidoptera and coleoptera. They are used at doses between 10 g and 300 g of active material per hectare. The products of formula I can also be used to combat premises insects, to combat particularly flies, mosquitoes and cockroaches. The products of formula I may also be used to combat parasitic insects of animals, for example, lice, particularly on cattle, sheep and fowls.

The invention also has particularly as its object insecticide compositions containing as active principle at least one of the compounds previously defined. The preferred insecticidal compositions contain as active principle (S) cyano-(3-phenoxy-4-fluorophenyl)-methyl 1R, cis 2,2-dimethyl-3-(2,2-diiodoethenyl)-cyclopropane-carboxylate and a 50-50 mixture of (S) cyano-1-(3-phenoxy-4-fluorophenyl)-methyl 1R, cis 2,2-dimethyl-3-(2,2-diiodoethenyl)-cyclopropane-carboxylate and (R) cyano 1-(3-phenoxy-4-fluorophenyl)-methyl 1S, cis 2,2-dimethyl-3-(2,2-diiodoethenyl)-cyclopropane-carboxylate. The insecticidal compositions of the invention preferably contain from 0.005% to 10% by weight of active material.

According to an advantageous way of operating, for use in premises, the insecticide compositions of the invention are utilized in the form of fumigating compositions. The insecticide compositions of the invention may then be constituted advantageously, for the non-active part, of a combustible serpentine or of an incombustible fibrous substrate. In this latter case, the fumigant obtained after incorporation of the active material is placed on a heating apparatus such as an electro-emanator. If an insecticide serpentine is used, the inert support can be, for example, composed of pyrethrum marc, Tabu powder (or Machilus Thunbergii leaf powder), pyrethrum stem powder, cedar leaf powder, wood powder (such as pine sawdust), starch and coconut shell powder. The quantity of active material can then be, for example, from 0.03 to 1% by weight. If an incombustible fibrous support is used, the quantity of active material can then be, for example, from 0.03 to 95% by weight.

The compositions of the invention for use in premises can also be obtained by preparing an atomizable oil based on the active principle, this oil soaking the wick of a lamp and then being submitted to combustion. The concentration of active principle incorporated in the oil is preferably from 0.03 to 95% by weight.

The invention compounds can also be used to combat parasitic acariens of vegetation and the biological study further on clearly shows the remarkable acaricide properties of the products of Example 4. The compositions may also be used to combat parasitic nematodes of vegetation. Therefore, the invention also has as its object acaricide compositions as well as nematocide compositions containing as active principle at least one compound of formula I. The acaricide and nematocide compositions can be presented in particular in the form of powders, granules, suspensions, emulsions, and solutions.

For acaricide use, it is preferred to use wettable powders for foliar atomization containing from 1 to 80% of active principle, or liquids for foliar atomization containing from 1 to 500 g/l of active material. Powders for foliar powdering can also be used containing from 0.05 to 3% of active material. For nematocide use, it is preferred to use liquids for soil treatment containing from 300 to 500 g/l of active principle. The acaricide and nematocide compounds of the invention are used preferably at quantities between 1 and 100 g of active material per hectare.

The compounds of formula I can also be used to combat parasitic acariens of animals such as ticks and particularly ticks of the Boophilus species, those of the Hyalomnia species, those of the Amblyomnia species and those of the Rhipicephalus species, or to combat all sorts of mites and particularly sarcoptic mites, psoroptic mites and chorioptic mites. Therefore, the invention also has as its subject compositions used in combatting parasitic acariens of warm-blooded anaimals, characterized in that they contain at least one product defined above.

Those compositions can be administered externally by vaporizing, by shampooing, by bath, or by painting on. They can also be administered by painting on the backbone by the so-called "pour on" method and they can also be administered by the digestive route.

When it is a matter of combatting parasitic acariens of animals, the compositions are very often incorporated in alimentary compositions in association with a nutritive mixture suitable for feeding the animal which nutritive mixture will vary according to the animal species. It can contain cereals, sugars and seeds, soya, groundnut and sunflower cakes, meals of animal origin, for example, fish meals, synthetic amino acids, mineral salts, vitamins and anti-oxidants. Thus, the invention also has as its object compositions intended for animal feeding containing as active principle at least one of the products of formula I.

To increase the biological activity of the products of the invention, they can have added to them standard synergists used in similar cases such as 1-(2,5,8-trioxadodecyl)-2-propyl-4,5-methylenedioxy benzene (or piperonyl butoxide) or N-(2-ethylheptyl)-bicyclo[2,2,1]-5-hepten-2,3-dicarboximide, or piperonyl-bis-2-(2'n-butoxyethoxy)-ethylacetal (or tropital).

The invention also has as its object compositions endowed with insecticide, acaricide or nematocide activity characterized in that they contain as active material, on the one hand, at least one of the compounds of formula I, and on the other hand, at least one of the pyrethrinoid esters selected from the group consisting of esters of allethrolones, of 3,4,5,6-tetrahydrophthalimidomethyl alcohol, of 5-benzyl-3-furyl methyl alcohol, of 3-phenoxy-benzyl alcohol and α-cyano-3-phenoxy benzyl alcohols, with chrysanthemic acids, by the esters of 5-benzyl-3-furyl methyl alcohol with 2,2-dimethyl-3-(2-oxo-3-tetrahydrothiophenylidenemethyl)-cyclopropane-1-carboxylic acids, by the esters of 3-phenoxy-benzyl alcohol and α-cyano-3-phenoxy-benzyl alcohols with 2,2-dimethyl-3-(2,2-dichlorovinyl)-cyclopropane-1-carboxylic acids, by the esters of α-cyano-3-phenoxy-benzyl alcohols with 2,2-dimethyl-3-(2,2-dibromovinyl)-cyclopropane-1-carboxylic acids, by the esters of 3-phenoxy-benzyl alcohol with 2-parachlorophenyl-2-isopropyl acetic acids, by the esters of allethrolone, 3,4,5,6-tetrahydrophthalimidomethyl alcohol, of 5-benzyl-3-furyl-methyl alcohol, of 3-phenoxybenzyl alcohol and α-cyano-3-phenoxy-benzyl alcohols with 2,2-dimethyl-3-(1,2,2,2-tetrahaloethyl)-cyclopropane-1-carboxylic acids, in which "halo" represents a fluorine, chlorine or bromine atom, it being understood that the compounds I can exist in all their possible stereo-isomeric forms, as can the acid and alcohol moiety of the above pyrethrinoid esters. The said compositions are of particular interest because of their wider range of parasitic activity due to the polyvalency of their action and having a synergistic effect in some instances.

In the following examples there are described several preferred embodiments to illustrate the invention. However, it should be understood that the invention is not intended to be limited to the specific embodiments.

EXAMPLE 1

1,1-dimethylethyl 1R, trans 2,2-dimethyl-3-(2,2-diiodoethenyl)-cyclopropane-carboxylate 10.1 g of triphenyl phosphine and 180 ml of methylene chloride were mixed together, at 0° C. and 10 g of tetraiodomethane were introduced with stirring for 20 minutes at 0° C. A solution of 1.9 g of tert.-butyl 1R, trans, 3-formyl-2,2-dimethyl-cyclopropane-carboxylate in 20 ml of methylene chloride was added progressively with stirring for 20 hours at +20° C. After concentrating to dryness by distilling under reduced pressure, the residue was chromatographed over silica and eluted with a mixture of methylene chloride and ethyl acetate (1/1), then with a mixture of methylene chloride and hexane (3/7) to obtain 2.5 g of 1,1-dimethylethyl 1R, trans 2,2-dimethyl-3-(2,2-diiodoethenyl)-cyclopropane-carboxylate.

IR Spectrum (chloroform): Absorption at 1,710 cm$^{-1}$

of the tert-butyl ester: 1,370 cm$^{-1}$ —CH$_3$, 1,190 cm$^{-1}$ C—O—C.

NMR Spectrum (deuterochloroform): Peaks at 1.2 to 1.3 ppm (hydrogens of the twinned methyls), Peaks at 1.47 ppm (hydrogens of tert-butyl); Peaks at 1.55 to 1.65 ppm (hydrogens of cyclopropane); Peaks from 1.83 to 2.03 ppm (3-hydrogen of cyclopropane); and Peaks at 6.75 to 6.87 ppm (hydrogen of ethenyl).

EXAMPLE 2

1,1-dimethylethyl 1R, cis 2,2-dimethyl-3-(2,2-diiodoethenyl)-cyclopropane-carboxylate 10.1 g of triphenyl phosphine and 180 ml of methylene chloride were mixed together at 0° C. and 10 g of tetraiodomethane were introduced with stirring for 15 minutes at 0° C. At 0° C., a solution of 1.9 g of tert-butyl 1R, cis 3-formyl-2,2-dimethyl-cyclopropane-carboxylate in 20 ml of methylene chloride was introduced progressively, with stirring for 30 hours at +20° C. After filtering and concentrating the filtrate to dryness by distillation and under reduced pressure, the residue was chromatographed over silica and eluted with a mixture of ethyl acetate and methylene chloride (1/1), then with a mixture of methylene chloride and hexane (3/7) to obtain 1.01 g of 1,1-dimethylethyl 1R, cis 2,2-dimethyl-3-(2,2-diiodoethenyl)-cyclopropane-carboxylate.

IR Spectrum (chloroform): Absorption at 1,710 cm$^{-1}$ attributed to the

of the ester, 1,368 cm$^{-1}$ attributed to the methyl of the tert-butyl, 1,160 cm$^{-1}$ attributed to C—O—C.

NMR Spectrum (deuterochloroform): Peaks at 1.25 ppm (hydrogens of twinned methyls), Peaks at 1.47 ppm (hydrogens of tert-butyl); Peaks at 1.58 and 1.85 ppm (hydrogens in positions 1 and 3 of cyclopropane); and Peaks at 7.32 to 7.4 ppm (hydrogen of ethenyl).

EXAMPLE 3

(S) cyano-(3-phenoxy phenyl)-methyl 1R, trans 2,2-dimethyl-3-(2,2-diiodoethenyl)-cyclopropane-carboxylate STEP A: 1R, trans 2,2-dimethyl-3-(2,2-diiodoethenyl)-cyclopropane-carboxylic acid 10.1 g of triphenyl phosphine and 200 ml of methylene chloride were mixed together and at 0° C., 10.25 g of tetraiodomethane were added, with stirring for 15 minutes at 0° C. A solution of 1.9 g of 1,1-dimethylethyl of 3-formyl-2,2-dimethyl-cyclopropane-carboxylate in 20 ml of methylene chloride was introduced progressively, with stirring for 17 hours at +20° C. 1.25 g of electrolytic zinc were added with stirring for 10 minutes, followed by filtering and concentrating the filtrate to dryness by distilling under reduced pressure. The residue was chromatographed over silica, and eluted with methylene chloride, then with a mixture of methylene chloride and ethyl acetate (1/1) to obtain 2.6 g of 1R, trans 2,2-dimethyl-3-(2,2-diiodoethenyl-cyclopropane carboxylic acid melting at 100° C.

| IR Spectrum (chloroform): | | |
|---|---|---|
| Absorption at 3,505 cm$^{-1}$, | attributed to —OH, | monomer and dimer; |
| 1,737 cm$^{-1}$ | attributed to —C— ‖ O | monomer acid |

IR Spectrum (chloroform):

NMR Spectrum (deuterochloroform): Peaks at 1.22 to 1.33 ppm (hydrogens of twinned methyls); Peaks at 1.64 to 1.73 ppm (1-hydrogen of cyclopropane); Peaks at 1.90 to 1.99 ppm and 2.02 to 2.12 ppm (3-hydrogen of cyclopropane); Peaks at 6.74 to 6.85 ppm (hydrogen of ethenyl); and Peak at 10.55 ppm (hydrogen of carboxyl).

STEP A₂: 1R, trans 2,2-dimethyl-3-(2,2-diiodoethenyl)-cyclopropane-carboxylic acid 2.2 g of 1,1-dimethylethyl 1R, trans 2,2-dimethyl-3-(2,2-diiodoethenyl)-cyclopropane-carboxylate and 20 ml of toluene were mixed together at reflux and then 200 mg of p-toluene sulfonic acid were introduced. The mixture was refluxed for 15 minutes and was then cooled and concentrated to dryness by distilling under reduced pressure. The residue was chromatographed over silica and eluted with a mixture of hexane and ethyl acetate (6/4) to obtain 1.6 g of 1R, trans 2,2-dimethyl-3-(2,2-diiosodethenyl)-cyclopropane-carboxylic acid melting at 101° C.

STEP B: (S) cyano-(3-phenoxy-phenyl)-methyl 1R, trans 2,2-dimethyl-3-(2,2-diiodoethenyl)-cyclopropane-carboxylate 1.9 g of 1R, trans 2,2-dimethyl-3-(2,2-diiodoethenyl)-cyclopropane-carboxylic acid, 1.3 g of (S) α-cyano-3-phenoxy-benzyl alcohol, 20 mg of 4-dimethylamino-pyridine and 20 ml of methylene chloride were mixed together, and at +5° C., a solution of 1.45 g of dicyclohexyl-carbodiimide in 10 ml of methylene chloride was introduced progressively. After taking to +20° C. and filtering, the filtrate was concentrated to dryness by distilling under reduced pressure. The residue was chromatographed over silica and eluted with a mixture of hexane and ethyl acetate (9/1) to obtain 1.95 g of (S) cyano-(3-phenoxy-phenyl)-methyl 1R, trans 2,2-dimethyl-3-(2,2-diiodoethenyl)-cyclopropane-carboxylate.

IR Spectrum (chloroform): Absorption at 1,740 cm⁻¹ attributed to the

of the ester 1,585 cm⁻¹ and 1,485 cm⁻¹ attributed to the aromatic fraction of the type

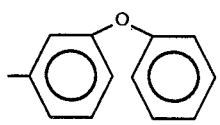

NMR Spectrum (deuterochloroform): Peaks at 1.2 to 1.25 ppm (hydrogens of twinned methyls); Peaks at 1.67 to 1.76 ppm (1-hydrogen of cyclopropane); Peaks at 1.93 to 2.15 ppm (3-hydrogen of cyclopropane); Peaks at 6.38 ppm (hydrogen on the same carbon as the CN); Peaks at 6.75 to 6.87 ppm (hydrogen of ethenyl); and Peaks from 6.92 to 7.58 ppm (hydrogens of aromatic nuclei).

EXAMPLE 4

(S) cyano-1-(3-phenoxy-4-fluorophenyl)-methyl 1R, trans 2,2-dimethyl-3-(2,2-diiodoethenyl)-cyclopropane-carboxylate 1.5 g of 1R, trans 2,2-dimethyl-3-(2,2-diiodoethenyl)-cyclopropane carboxylic acid, 855 mg of (S) cyano-3-phenoxy-4-fluorophenylmethyl alcohol, 15 mg of 4-dimethylamino pyridine and 15 ml of methylene chloride were mixed together and then, at 5° C., a solution of 870 mg of dicyclohexylcarbodiimide in 5 ml of methylene chloride was introduced. The mixture was stirred for 2 hours at +20° C. and then filtered and the filtrate was concentrated to dryness by distilling under reduced pressure. The residue was chromatographed over silica and eluted with a mixture of methylene chloride and hexane (45/55) to obtain 1.4 g of (S) cyano-1-(3-phenoxy-4-fluorophenyl)-methyl 1R, trans 2,2-dimethyl-3-(2,2-diiodoethenyl)-cyclopropane-carboxylate.

IR Spectrum (chloroform):

1,610 cm⁻¹,
1,589 cm⁻¹,
1,512 cm⁻¹,
1,490 cm⁻¹,

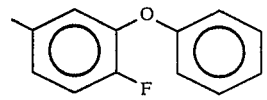

attributed to the aromatic fraction of the type

NMR Spectrum (deuterochloroform): Peaks at 1.19 to 1.22 ppm (hydrogens of twinned methyls); Peaks at 1.65 to 1.74 ppm (1-hydrogen of cyclopropane); Peaks at 1.92 to 2.12 ppm (3-hydrogen of cyclopropane); Peak at 6.33 ppm (hydrogen on the same carbon as CN); Peaks at 6.73 to 6.85 ppm (hydrogen of ethenyl); Peaks from 6.88 to 7.5 ppm (hydrogens of aromatic nuclei).

EXAMPLE 5

(S)-cyano-1-(3-phenoxy-4-fluorophenyl)-methyl 1R, cis 2,2-dimethyl-3-(2,2-diiodoethenyl)-cyclopropane-carboxylate STEP A: 1R, cis 2,2-dimethyl-3-(2,2-diiodoethenyl)-cyclopropane carboxylic acid 930 mg of tert-butyl 1R, cis 2,2-dimethyl-3-(2,2-diiodoethenyl)-cyclopropane-carboxylate, 90 mg of p-toluene sulfonic acid and 10 ml of toluene were mixed together and the reaction mixture was refluxed for 15 minutes, then cooled. After concentrating to dryness by distilling under reduced pressure, the residue was chromatographed over silica and eluted with a mixture of ethyl acetate and hexane (3/7) to obtain 770 mg of 1R, cis 2,2-dimethyl-3-(2,2-diiodoethenyl)-cyclopropane carboxylic acid melting at 140° C.

IR Spectrum (chloroform): Absorption at 3,505 cm⁻¹, attributed to —OH, monomer and dimer. 1,735 cm⁻¹,

monomer acid, 1,697 cm$^{-1}$

dimer acid.

NMR Spectrum (deuterochloroform): Peak at 1.3 ppm (hydrogens of twinned methyls), Peaks at 1.63 and 1.98 ppm (1 and 3 hydrogens of cyclopropane; Peaks from 7.13 to 7.42 ppm (hydrogen of ethenyl).

STEP B: (S)
-cyano-1-(3-phenoxy-4-fluorophenyl)-methyl 1R, cis 2,2-dimethyl-3-(2,2-diiodoethenyl)-cyclopropane carboxylate 750 mg of 1R, cis 2,2-dimethyl-3-(2,2-diiodoethenyl)-cyclopropane carboxylic acid, 440 mg of (S) α-cyano-3-phenoxy-4-fluorophenyl)-methyl alcohol, 7.5 mg of 4-dimethylamino pyridine and 7.5 ml of methylene chloride were mixed together and then at +5° C., a solution of 430 mg of dicyclohexylcarbodiimide in 2.5 ml of methylene chloride were added progressively. The mixture was stirred for 2 hours at +20° C. and then filtered and the filtrate was concentrated to dryness by distilling under reduced pressure. The residue was chromatographed over silica and eluted with a mixture of methylene chloride and hexane (1/1), and after washing by triturating in hexane, 700 mg of (S) -cyano-1-(3-phenoxy-4-fluorophenyl)-methyl 1R, cis 2,2-dimethyl-3-(2,2-diiodoethenyl)-cyclopropane-carboxylate melting at 98° C. were obtained.

| IR Spectrum (chloroform): | |
|---|---|
| Absorption at 1,742 cm$^{-1}$, | attributed to 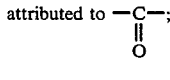 |
| 1,610 cm$^{-1}$, 1,390 cm$^{-1}$, 1,510 cm$^{-1}$, 1,490 cm$^{-1}$, | 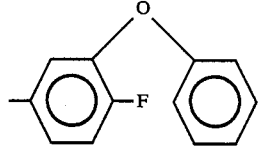 | attributed to the aromatic fraction of type

NMR Spectrum (deuterochloroform): Peaks at 1.17 to 1.25 ppm (hydrogens of twinned methyls); Peaks at 1.78 and 1.98 ppm (1 and 3-hydrogens of cyclopropane); Peak at 6.34 ppm (hydrogen on the same carbon as CN); Peaks at 6.9 to 7.53 ppm (hydrogens of aromatic neuclei and hydrogen of ethenyl).

EXAMPLE 6

(S) -cyano-(3-phenoxy-phenyl)-methyl 1R,cis 2,2-dimethyl-3-(2,2-diiodoethenyl)-cyclopropane-carboxylate Using the procedure of Step B of Example 3, 1.9 g of 1R,cis 2,2-dimethyl-3-(2,2-diiodoethenyl)-cyclopropane carboxylic acid (obtained as described in Example 5) were reacted to obtain 1.95 g of crude product which was chromatographed over silica and eluted with a mixture of methylene chloride and ethyl acetate (1/1), then washing by triturating in acetonitrile. After filtering, washing with ether and crystallization from ethyl acetate, 1.7 g of (S) -cyano-(3phenoxy-phenyl)-methyl 1R,cis 2,2-dimethyl-3-(2,2-diiodoethenyl)-cyclopropane-carboxlate melting at 130° C. were obtained.

IR Spectrum (chloroform): Absorption at 1,742 cm$^{-1}$, attributed to

1,587 cm$^{-1}$ and 1,487 cm$-1$, aromatic fraction of the type

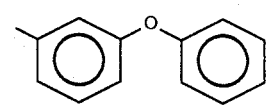

NMR Spectrum (deuterochloroform): Peaks at 1.22 to 1.29 ppm (hydrogens of twinned methyls); Peaks at 1.82 to 2.09 ppm (1- and 3-hydrogens of cyclopropane); Peak at 6.43 ppm (hydrogen on the same carbon as CN); Peaks from 6.98 to 7.6 ppm (hydrogens of aromatic nuclei and hydrogen of ethenyl).

EXAMPLE 7

[2-methyl-(1,1'-biphenyl)-3-yl]-methyl 1R,trans 2,2-dimethyl-3-(2,2diiodoethenyl)-cyclopropane-carboxylate 0.83 g of 1R,trans 2,2-dimethyl-3-(2,2-diiodoethenyl)-cyclopropane carboxylic acid, 10 ml of methylene chloride, 10 mg of 4,4-dimethylamino-pyridine and 0.43 g of [2-methyl-(1,1'-biphenyl)-3-yl]-methyl alcohol were mixed together and then at 20° C., 0.447 g of dicyclohexylcarbodiimide were added all at once. The urea formed was eliminated by filtering and the filtrate was concentrated to dryness by distilling under reduced pressure. The residue was chromatographed over silica and eluted with a mixture of hexane and ethyl acetate (9/1) to obtain 0.95 g of [2-biphenyl)-3-yl]-methyl 1R,trans 2,2-dimethyl-3-(2,2-diiodoethenyl)-cyclopropane-carboxylate.

| IR Spectrum (chloroform): | |
|---|---|
| C ester  | at 1,720 cm$^{-1}$ |
| aromatic | at 1,590 cm$^{-1}$ |
| aromatic | at 1,498 cm$^{-1}$ |

NMR Spectrum (CHCl$_3$): (hydrogens of twinned methyls): 1.22 to 1.32 ppm, (1-hydrogen of cyclopropyl): 1.71 to 1.8 ppm, (3-hydrogen of cyclopropyl): 1.99 to 2.13 ppm, (hydrogen of 2-methyl): 2.25 ppm, (hydrogen of —CO$_2$ CH$_2$ 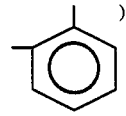 ): 5.23 ppm (ethylene hydrogen): 6.77 to 6.88 ppm, (aromatic hydrogens): 7.22 to 7.56 ppm.

EXAMPLE 8

[2-methyl-(1,2'-biphenyl)-3-yl]methyl 1R,cis 2,2-dimethyl-3-(2,2-diiodoethenyl)-cyclopropane-carboxylate 1 g of 1R,cis 2,2-dimethyl-3-(2,2-diiodoethenyl)-cyclopropane carboxylic acid, 20 ml of methylene chloride, 10 mg of 4-dimethylamino-pyridine and 0.55 g of [2-methyl-(1,1'-biphenyl)-3-yl]-methyl alcohol were mixed together and 0.58 g of dicyclohexylcarbodiimide were added at at once. After stirring for 2 hours at 20° C., the urea formed was eliminated by filtering. The organic phase was washed with water and concentration by dryness by distilling under reduced pressure and the residue was chromatographed over silica. Elution with a mixture of hexane and ethyl acetate (9/1) yielded 1.3 g of [2-methyl-(1,1'-biphenyl)-3-yl]-methyl 1R,cis 2,2-dimethyl-3-(2,2-diiodoethenyl)-cyclo-propane-carboxylate.

| IR Spectrum (CHCl₃) | |
|---|---|
| C ester ‖ O | at 1,720 cm$^{-1}$ |
| aromatic | at 1,585 cm$^{-1}$ |
| aromatic | at 1,495 cm$^{-1}$ |

NMR Spectrum (CDCl₃): (hydrogens of twinned methyls): 1.26 to 1.28 ppm; (1- and 3-hydrogens of cyclopropyl): 1.55 to 2.02 ppm; (hydrogen of 2-methyl): 2.31 ppm; (hydrogen of

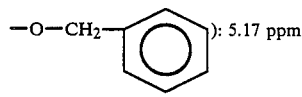): 5.17 ppm (aromatic hydrogens and ethylene proton): 7.15 to 7.48 ppm.

| Analysis: C$_{22}$H$_{22}$O$_2$I$_2$; molecular weight = 572.228 | | | | | | |
|---|---|---|---|---|---|---|
| Calculated: | % C | 46.18 | % H | 3.87 | % I | 44.35 |
| Found: | | 47.2 | | 4.0 | | 42.4 |

EXAMPLE 9

1,1-dimethyl-ethyl 1S, cis 2,2-dimethyl-3-(2,2-diiodoethenyl)-cyclo-propane-carboxylate At 0° C., g of tetraiodomethane were introduced into a solution of 10.1 g of triphenyl-phosphine and 180 ml of methylene chloride and after stirring for 20 minutes at 0° C., 1.9 of 1,1-dimethyl-ethyl 1S, cis 2,2-dimethyl-3-formyl cyclopropane-carboxylate and 20 ml of methylene chloride were introduced and stirring was maintained for 17 hours. After washing, drying and evaporating to dryness, a residue was obtained which was taken up in 250 ml of isopropyl ether and then filtered. The filtrate was evaporated to obtain 3.85 g of product which was chromatographed over silica and eluted with a mixture of methylene chloride and hexane (3/7) to obtain 2.3 g of 1,1-dimethyl-ethyl 1S,cis 2,2-dimethyl-3-(2,2-diiodoethenyl)-cyclopropane-carboxylate melting at 54° C.

EXAMPLE 10

R -cyano1-(3-phenoxy-4-fluorophenyl)-methyl 1S,cis 2,2-dimethyl-3-(2,2-diiododethenyl)-cyclopropane-carboxylate STEP A: 1S,cis 2,2-dimethyl-3-(2,2-diiodoethenyl)-cyclopropane-carboxylic acid A solution of 2.15 g of the product of Step A, 10 ml of toluene and 200 mg of p-toluene sulfonic acid was heated to reflux and then cooled and diluted with 30 ml of ethyl acetate. The organic phases were washed and dried and evaporated to dryness under reduced pressure to obtain 1.85 g of product which was chromatographed over silica and eluted with a mixture of hexane and ethyl acetate (7/3) to obtain 1.55 g of 1S,cis 2,2-dimethyl-3-(2,2-diiodoethenyl)-cyclo-propane carboxylic acid melting at 139° C.

STEP B: R -cyano1-(3-phenoxy-4fluorophenyl)-methyl 1S, cis 2,2-dimethyl-3-(2,2-diiodoethenyl)-cyclopropane carboxylate At 0° C., 460 mg of dicyclohexylcarbodiimide in 5 ml of methylene chloride were introduced into a solution of 0.8 g of 1S,cis 2,2-dimethyl-3-(2,2-diiodoethenyl)-cyclopropane carboxylic acid, 458 mg of (R) αcyano-3-phenoxy-4-fluorophenyl)-methyl alcohol, 9 mg of 4-diemthylamino-pyridine and 8 ml of methylene chloride. After filtering, the solvent was chromatographed over silica and eiluted with a mixture of methylene chloride and hexane (1/1) to obtain a resin which was chromatographed again to obtain 780 mg of R -cyano-1-(3-phenoxy-4-fluorophenyl)-methyl 1S,cis 2,2-dimethyl-3-(2,2-diiodoethenyl)-cyclopropane-carboxylate melting at 95° C. and having a specific rotation of $[\alpha]_D^{20} = -25° \pm 1(c=0.9\%\ CHCl_3)$.

NMR Spectrum: (hydrogen twinned methyls): 1.2 to 1.26 ppm; (1-and 3-hydrogens of cyclopropyl): 1.66 to 2 ppm; (hydrogen of ethylene): 6.95 to 7.57 ppm; (hydrogen on the same carbon as CN): 6.38 ppm.

EXAMPLE 11

50-50 mixture of (S) -cyano-1-(3-phenoxy-4-fluorophenyl)-methyl 1R,cis 2,2-dimethyl-3-(2,2-diiodoethenyl)-cyclopropane carboxylate and (R) -cyano-1-(3-phenoxy-4-fluorophenyl)-methyl 1S,cis 2,2-dimethyl-3-(2,2-diiiodoethenyl)-cyclopropane-carboxylate Using the above procedure, a mixture of 1R,cis 2,2-dimethyl-3-(2,2-diiodoethenyl)-cyclopropane carboxylic acid and its 1S,cis isomer and (RS) -cyano-1-(3-phenoxy-4-fluorophenyl)-methyl alcohol was reacted to obtain after separation by chromatography a 50-50 mixture of (S) -cyano-1-(3-phenoxy-4-fluorophenyl)-methyl 1R,cis 2,2-dimethyl-3-(2,2-diiodoethenyl)-cyclopropane carboxylate and (R) -cyano-1-(3-phenoxy-4-fluorophenyl)-methyl 1S,cis 2,2-dimethyl-3-(2,2-diiodoethenyl)cyclopropane-carboxylate melting at 104° C.

EXAMPLE 12

50-50 mixture of (S) -cyano-1-(3-phenoxy-phenyl)-methyl 1R,cis 2,2-dimethyl-3-(2,2-diiodoethenyl)-cyclopropane carboxylate and the (R) -cyano-1-(3-phenoxy-phenyl)-methyl 1S, cis 2,2-dimethyl-3-(2,2-diiodoethenyl)-cyclopropane carboxylate Using the procedure of Example 11, (RS) -cyano-1-(3-phenoxy-phenyl)-methyl alcohol was reacted to obtain 50-50 mixture of (S) -cyano-1-(3-phenoxy-phenyl)-methyl 1R,cis 2,2-dimethyl-3-(2,2-diiodoethenyl)-cyclopropane-carboxylate adn the (R) -cyano-1-(3-phenoxy-phenyl)-methyl 1S, cis 2,2-dimethyl-3-(2,2-diiodoethenyl)-cyclopropane carboxylate melting at 116° C.

EXAMPLES 13 to 22

Using the above procedure, the following products were prepared:
pentafluorophenyl-methyl, 1R,trans 2,2-dimethyl-3-(2,2-diiodoethenyl)-cyclopropane-carboxylate $[\alpha]_D = +4.5° \pm 0°5 (c=1.5\% \text{ CHCl}_3)$
1-(3-phenoxyphenyl)-methyl 1R, 2,2-dimethyl-3-(2,2-diiodoethenyl)-cyclopropane-carboxylate $[\alpha]_D = +8°5 \pm 0°5 (c=1.5\% \text{ CHCl}_3)$
(S) 3-(2-propenyl)-2-methyl-4-oxo-2cyclopentenyl) 1R, trans 2,2-dimethyl-3-(2,2-diiodoethenyl)-cyclopropane carboxylate $[\alpha]_D = -2° \pm 1° (c=1\% \text{ CHCl}_3)$
methyl-1-(6-phenoxy-2-pyridyl)-methyl, 1R, 2,2-dimethyl-3-(2,2-diiodoethenyl-cyclopropane-carboxylate $[\alpha]_D = +25°5 \pm 1° (c=1\% \text{ CHCl}_3)$
cyano-1-(6-phenoxy-2-pyridyl)-methyl 1R,trans 2,2-dimethyl-3-(2,2-diiodoethenyl)-cyclopropane-carboxylate $[\alpha]_D = +16° \pm 0°5 (c=1.5\% \text{ CHCl}_3)$
(S) 3-(2-propenyl)-2-methyl-4oxo-2-cyclopentenyl 1R,cis 2,2-dimethyl-3-(2,2diiodoethenyl)-cyclopropane carboxylate $[\alpha]_D = +13° \pm 1°5 (c=0.6\% \text{ CHCl}_3)$
cyano-1-(6-phenoxy-2-pyridyl)-methyl 1R,cis 2,2-dimethyl-3-(2,2diiodoethenyl)-cyclopropane carboxylate $[\alpha]_D = -5° \pm 1° (c=0.9\% \text{ CHCl}_3)$
methyl-1-(6-phenoxy-2-pyridyl)-methyl 1R,cis 2,2-dimethyl-3-(2,2-diiodoethenyl)-cyclopropane-carboxylate $[\alpha]_D = +7° \pm 1° (c=1\% \text{ CHCl}_3)$
1-(3-phenoxy-phenyl)-methyl 1R,cis 2,2-dimethyl-3-(2,2-diiodoethenyl)-cyclopropane carboxylate $[\alpha]_D = -11° \pm 1° (c=1\% \text{ CHCl}_3)$
pentafluorophenyl-methyl 1R,cis 2,2-dimethyl-3-(2,2-diiodoethenyl)-cyclopropane carboxylate $[\alpha]_D = -14° \pm 0°5 (c=2\% \text{ CHCl}_3)$.

EXAMPLE 23

Preparation of a soluble concentrate was made from a homogeneous mixture of:
Product of Example 5: 0.25 g
Piperonyl butoxide: 1 g
Tween 80: 0.25 g
Topanol A: 0.1 g
Water: 98.4 g

EXAMPLE 24

Preparation of an emulsifiable concentrate was made by mixing intimately:
Product of Example 5: 0.015 g
Piperonyl butoxide: 0.5 g
Topanol A: 0.1 g
Xylene: 95.885 g
Tween 80: 3.5 g

EXAMPLE 25

Preparation of an emulsifiable concentrate was made by mixing homogeneously:
Product of Example 5: 1.5 g
Tween 80: 20 g
Topanol A: 0.2 g
Xylene: 78.4 g

EXAMPLE 26

Preparation of a fumigating composition was made by mixing homogeneously:
Product of Example 5: 0.25 g
Tabu powder: 25 g
Cedar leaf powder: 40 g
Pine wood powder: 33.75 g
Brilliant green: 0.5 g
p. nitrophenol: 0.5 g

EXAMPLE 27

Preparation of a soluble concentrate was made from a homogeneous mixture of:
Product of Example 11: 0.25 g
Piperonyl butoxide: 1 g
Tween 80: 0.25 g
Topanol A: 0.1 g
Water: 98.4 g

EXAMPLE 28

Preparation of an emulsifiable concentrate was made by mixing initimately:
Product of Example 7: 0.015 g
Piperonyl butoxide: 0.5 g
Topanol A: 0.1 g
Xylene: 95.985 g
Tween 80: 3.5 g

EXAMPLE 29

Preparation of an emulsifiable concentrate was made by mixing homogeneously:
Product of Example 8: 1.5 g
Tween 80: 20 g
Topanol A: 0.2 g
Xylene: 78.4 g

BIOLOGICAL STUDY

A. Study of the Lethal Effect on Domestic Flies

The test insects were female houseflies aged 4 to 5 days and the operation was done by topical application of 1 μl of acetone solution of the product on the dorsal thorax of the insects with an Arnold micro-manipulator. 50 individuals were used per dose and per treatment. The results obtained, expressed in $LD_{50}$ on the dose in nanograms necessary to kill 50% of the insects, was the following:

| Product of Example | LD$_{50}$ in ng per individual |
|---|---|
| 4 | 3.8 |
| 5 | 1.6 |
| 6 | 2.0 |
| 11 | 1.92 |

CONCLUSION

In the test used, the products of Examples 4,5,6 and 11 showed a remarkable activity.

B. Study of the Activity by Tarsal Contact on the Cockroach

The insects tested were cockroach males (Blatella germanical) and the operation was done by depositing an acetone solution of known concentration on the bottom of a Petri dish, 20 ml in diameter. After drying, 20 male cockroaches per concentration were left there for 1 hour, after which the insects were transferred on to a healthy medium and the mortality was checked at 24 hours, 48 hours, 3 and 5 days. The results expressed as lethal concentration 50 (LC$_{50}$) are as follows:

| Product of Example | LC$_{50}$ in mg/m$^2$ |
|---|---|
| 3 | 0.15 |
| 4 | 0.152 |
| 5 | 0.025 |
| 6 | 0.062 |
| 11 | 0.121 |

CONCLUSION

In the test used, the products of Examples 3,4,5,6 and 11 showed a remarkable activity.

C. Study of the Shock Activity on Houseflies

The test insects were female houseflies aged from 4 to 5 days and the operation was done by direct atomization in a Kearns and March chamber using a mixture of equal volumes of acetone and isopar L as solvent (quantity of solution used 2×0.2 cm$^3$). About 50 insects were used per dose of treatment and checks were made every minute up to 10 minutes, then at 15 minutes, and the KT$_{50}$ was determined by the usual methods. The following results were obtained:

| Product of Example | KT$_{50}$ in minutes - concentration 1 g/l |
|---|---|
| 3 | 6.9 |
| 4 | 5.3 |
| 5 | 6.1 |
| 6 | 6.4 |
| 11 | 6.9 |

CONCLUSION

In the test used, the products of Examples 3,4,5,6 and 11 present a good activity.

D. Study of the Lethal Effect on Larvae of Spodoptera Littoralis

The trials were carried out by topical application of an acetone solution of the product under test with an Arnold micro-manipulator on the dorsal thorax of the larvae and 15 larvae were used per dose of the product under test. The larvae used were larvae of the fourth larval stage, i.e., aged about 10 days when they were raised to 24° C. and 65% relative humidity. After treatment, the individuals were placed on an artificial nutritive medium (Poitout's medium) and mortality check was made 48 hours after treatment.

| Product of Example | LD$_{50}$ in ng per individual |
|---|---|
| 5 | 1.16 |
| 11 | 4.8 |

CONCLUSION

The product of Examples 5 and 11 in the test used were endowed with a remarkable activity.

E. Study of the Lethal Effect on Acanthoscelides Obtectus

The trials were made by topical application in a similar manner to that used for the larvae of Spodoptera littoralis and the following results were obtained:

| Product of Example | LD$_{50}$ in ng per individual |
|---|---|
| 4 | 11.7 |
| 5 | 6.1 |
| 6 | 11.3 |
| 11 | 10.7 |

CONCLUSION

In the test used, the products of Examples 4,5,6 and 11 present a remarkable activity.

F. Study of the Lethal Effect on Aphis Cracivora

Using the procedure of test E on Aphis cracivora, the following results were obtained, expressed in lethal concentration 50 (LC$_{50}$).

| Product of Example | LC$_{50}$ |
|---|---|
| 11 | 0.46 mg/l |

CONCLUSION

In the test used, the product of Example 11 presented a good activity.

Various modifications of the compounds and method of the invention may be made without departing from the spirit or scope thereof and it is to be understood that the invention is intended to be limited only as defined in the appended claims.

What we claim is:

1. A compound selected from the group consisting of stereoisomers or mixtures of stereoisomers of compounds of the formula

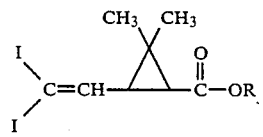

wherein R is

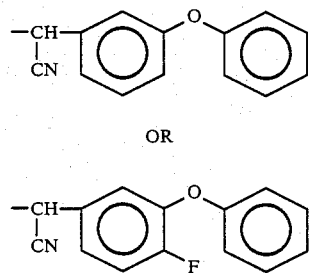

2. An insecticidal composition comprising an insecticidally effective amount of at least one compound of claim 1 and an inert carrier.

3. A method of combatting insects comprising contacting insects with an insecticidally effective amount of at least one compound of claim 1.

4. A compound of claim 1 selected from the group consisting of (S) cyano-(3-phenoxy-4-fluorophenyl)-methyl 1R,cis 2,2-dimethyl-3-(2,2-diiodoethenyl)-cyclopropane-carboxylate and a 50-50 of (S) cyano-1-(3-phenoxy-4-fluorophenyl)-methyl 1R, cis 2,2-dimethyl-3-(2,2-diiodoethenyl)-cyclopropane-carboxylate and (R) cyano-1-(3-phenxoy-4-fluorophenyl)-methyl, 1S,cis 2,2-dimethyl-3-(2,2-diiodoethenyl)-cyclopropane-carboxylate.

5. A composition of claim 2 wherein the active compound is selected from the group consisting of (S) cyano-(3-phenoxy-4-fluorophenyl)-methyl 1R,cis 2,2-dimethyl-3-(2,2-diiodoethenyl)-cyclopropane-carboxylate and a 50-50 mixture of (S) cyano-1-(3-phenoxy-4-fluorophenyl)-methyl 1R, cis 2,2-dimethyl-3-(2,2-diiodoethenyl)-cyclopropane-carboxylate and (R) cyano-1-(3phenoxy-4-fluorophenyl)-methyl 1S,cis 2,2-dimethyl-3-(2,2-diiodoethenyl)-cyclopropane-carboxylate.

6. A method of claim 3 wherein the active compound is selected from the group consisting of (S) cyano-(3-phenoxy-4-fluorophenyl)-methyl 1R,cis 2,2-dimethyl-3(2,2-diiodoethenyl)-cyclopropane-carboxylate and a 50-50 mixture of (S) cyano-1-(3-phenoxy-4-fluorophenyl)-methyl 1R, cis 2,2-dimethyl-3-(2,2-diiodoethenyl)-cyclopropane-carboxylate and (R) cyano-1-(3-phenoxy-4-fluorophenyl)-methyl 1S, cis 2,2-dimethyl-3-(2,2 -diiodoethenyl)-cyclopropane-carboxylate.

7. A method of combatting acariens comprising contacting acariens with an acaricidally effective amount of at least one compound of claim 1.

8. A method of combatting nematodes comprising contacting nematodes with a nematocidally effective amount of at least one compound of claim 1.

* * * * *